US007068924B2

(12) United States Patent
Watanabe et al.

(10) Patent No.: US 7,068,924 B2
(45) Date of Patent: Jun. 27, 2006

(54) STEAM GENERATOR

(75) Inventors: Shunichi Watanabe, Hikone (JP); Yasuhiro Adachi, Hikone (JP); Shingo Omura, Hikone (JP); Shigenori Kugumiya, Hikone (JP); Kazumi Okawa, Hikone (JP)

(73) Assignee: Matsushita Electric Works, Ltd., Osaka (JP)

( * ) Notice: Subject to any disclaimer, the term of this patent is extended or adjusted under 35 U.S.C. 154(b) by 0 days.

(21) Appl. No.: 11/151,279

(22) Filed: Jun. 14, 2005

(65) Prior Publication Data

US 2005/0276582 A1 Dec. 15, 2005

(30) Foreign Application Priority Data

Jun. 14, 2004 (JP) ............................. 2004-176160

(51) Int. Cl.
*A61L 9/03* (2006.01)

(52) U.S. Cl. ....................................... 392/386; 392/331

(58) Field of Classification Search ..................... None
See application file for complete search history.

(56) References Cited

U.S. PATENT DOCUMENTS

| | | | | |
|---|---|---|---|---|
| 2,095,051 A | | 10/1937 | Ronzi | |
| 3,775,589 A | * | 11/1973 | Camp | 392/337 |
| 3,796,857 A | * | 3/1974 | Henley et al. | 392/315 |
| 5,267,555 A | | 12/1993 | Pajalich | |
| 6,072,937 A | * | 6/2000 | Benade et al. | 392/336 |
| 6,302,331 B1 | | 10/2001 | Dvorsky et al. | |
| 2005/0150491 A1 | * | 7/2005 | Chen | 128/203.16 |

FOREIGN PATENT DOCUMENTS

| | | |
|---|---|---|
| GB | 466 204 A | 5/1937 |
| JP | 62-038180 A | 2/1987 |
| JP | 2001-190632 A | 7/2001 |

OTHER PUBLICATIONS

EPO Search Report mailed on Sep. 27, 2005.

* cited by examiner

*Primary Examiner*—Thor S. Campbell
(74) *Attorney, Agent, or Firm*—Rader, Fishman & Grauer PLLC

(57) ABSTRACT

A steam generator for efficiently generating fine steam particles is provided. Water supplied from a water tank is heated by a heater to generate steam in a steam chamber. The steam generator has a discharge generating portion, which is composed of a pair of electrodes, an intermediate electrode disposed therebetween, and a voltage applying unit for applying a voltage between the electrodes to generate discharges between the electrodes and the intermediate electrode. The steam generated in the steam chamber is exposed to the discharges, so that fine steam particles are efficiently sprayed out from the steam generator.

12 Claims, 6 Drawing Sheets

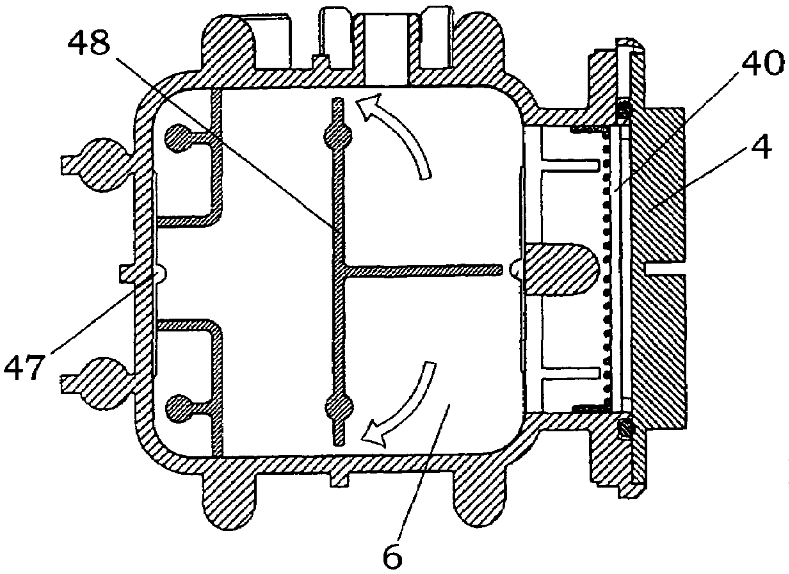
FIG. 14
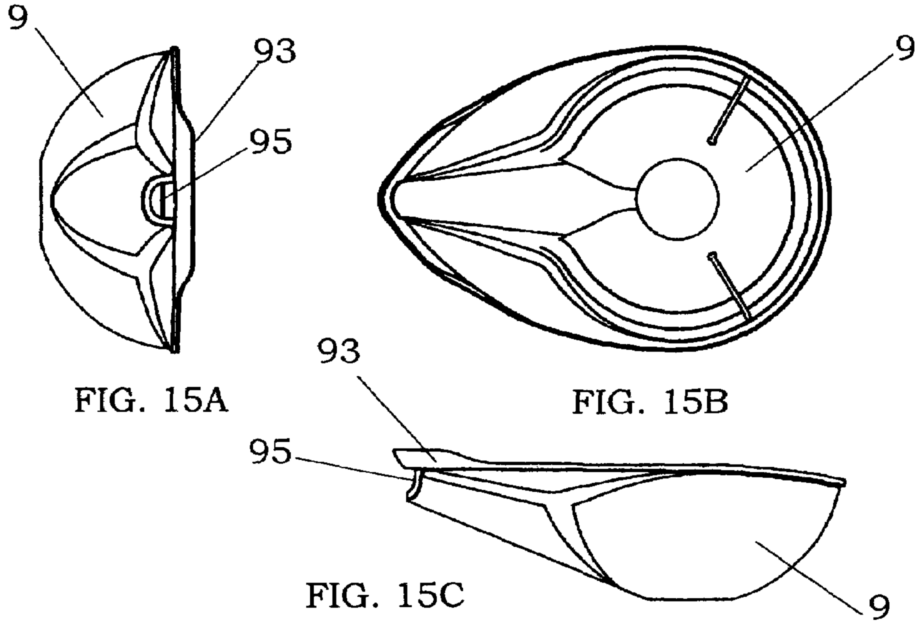
FIG. 15A
FIG. 15B
FIG. 15C
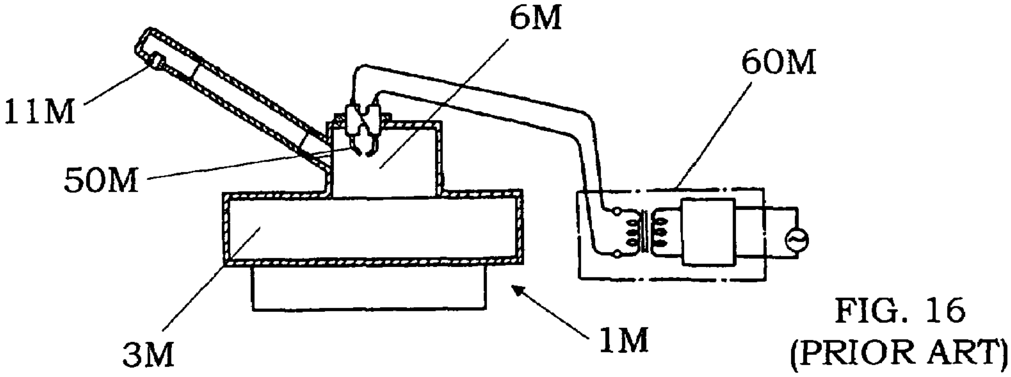
FIG. 16
(PRIOR ART)

STEAM GENERATOR

BACKGROUND OF THE INVENTION

1. Field of the Invention

The present invention relates to a steam generator for generating fine steam particles, which is preferably used as a skin care apparatus such as a facial steamer.

2. Disclosure of the Prior Art

In the past, a steam generator has been widely used as a humidifier for controlling indoor moisture levels, skin care apparatus such as facial steamer for moisturizing skin, facilitating cell metabolism and opening up pores to remove dead skin cells and clean the skin surface, and a steam inhaler for providing warm moist air to nose and throat and relieving or minimizing symptoms of hay fever and a cold.

For example, Japanese Patent Early Publication [kokai] No. 62-38180 discloses a facial steamer for generating ionized steam. As shown in FIG. 16, this facial steamer 1M is provided with a boiler room 3M with a heater for heating water to boiling to generate steam, a pair of electrodes 50M disposed in a steam channel 6M formed between the boiler room 3M and a steam outlet 11M, and a voltage applying unit 60M for applying a high voltage between the electrodes 50M to generate a discharge in the steam channel 6M. The steam generated in the boiler room 3M is exposed to the discharge in the steam channel 6M to obtain the ionized steam. It is believed that a skin care effect of the ionized steam is higher than the effect of normal steam.

However, the conventional facial steamer still has plenty of room for improvement from the viewpoint of further increasing the skin care effect.

SUMMARY OF THE INVENTION

Therefore, a primary object of the present invention is to provide a steam generator for efficiently generating fine steam particles, and achieving improvements in safety and skin care effect.

That is, the steam generator of the present invention comprises:

a housing having a steam outlet;

a liquid tank for storing a liquid;

a heater for heating the liquid provided from the liquid tank to generate steam in a chamber formed in the housing;

a steam channel extending from the chamber to the steam outlet;

at least one pair of electrodes disposed in the steam channel;

at least one intermediate electrode disposed between the electrodes; and a discharge generator configured to generate discharges between each of the electrodes and the at least one intermediate electrode.

According to the present invention, since steam particles generated in the steam chamber are exposed to the discharges generated between each of the electrodes and the intermediate electrode(s), amounts of fine condensation nuclei (for example, 0.5 to 2 μm) generated per unit time are increased, as compared with the case of simply exposing the steam particles to the discharge generated between the electrodes without using the intermediate electrode. It results in a remarkable effect of preventing growth of the steam particles. In addition, even when relatively large steam particles (for example, several ten microns) are generated in the steam chamber, they are efficiently turned to fine steam particles and then sprayed from the steam outlet. Therefore, it is possible to prevent a situation that large hot drops of water accidentally jetted out from the steam outlet, and improve safety of the steam generator. Furthermore, since a distance between the intermediate electrode and the electrode is shorter than the distance between the electrodes, a breakdown voltage needed to generate the discharge becomes small. As a result, this provides an energy-saving steam generator.

It is preferred that the discharge generator is a voltage applying means for applying a voltage between the electrodes, while keeping the intermediate electrode(s) in an electrically floating state. Alternatively, the voltage applying means may apply a voltage between the intermediate electrode(s) and the electrodes.

In addition, it is preferred that at least one of the electrodes has a stopper for preventing that a drop of the liquid flows into a discharge space between the intermediate electrode(s) and the electrode. When the liquid drop flows into a clearance (i.e., discharge space) between the intermediate electrode and the electrode, the discharge may become unstable or disappear. By the formation of the stopper, it is possible to stably maintain the discharges between the electrodes and the intermediate electrode(s).

It is also preferred that the intermediate electrode(s) is a plurality of intermediate electrodes, which are spaced from each other between the electrodes. In this case, since the number of discharges generated in the steam channel increases, it is possible to efficiently generate greater amounts of fine steam particles.

Another features of the present invention and advantages brought thereby will be more clearly understood from the following detail description, referring to the attached drawings.

BRIEF EXPLANATION OF THE DRAWINGS

FIG. 14 is a partially cross-sectional view showing a T-shaped partition wall disposed in the steam channel;

FIGS. 15A to 15C are front, top and side views of a protection cover for the steam beauty machine; and FIG. 16 is a cross-sectional view of a conventional steam generator used as a facial steamer.

DETAIL DESCRIPTION OF THE INVENTION

As a preferred embodiment of a steam generator of the present invention, a steam beauty machine is explained below in details, referring to the attached drawings.

Figure 1A:
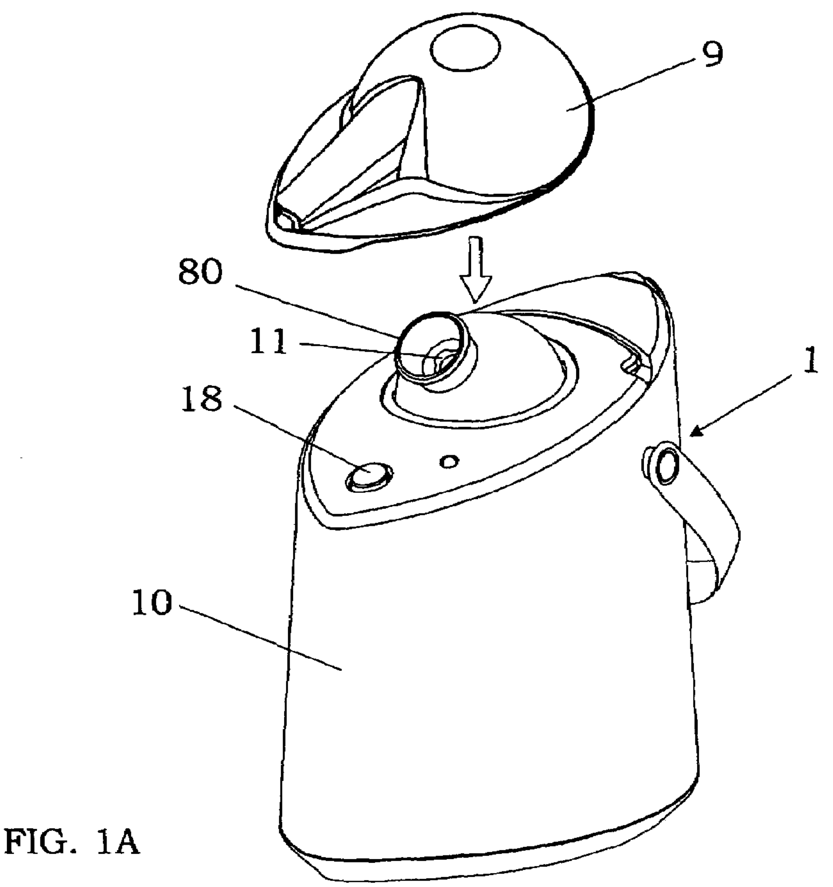
FIGS. 1A and 1B are perspective and cross-sectional views of a steam beauty machine as a preferred embodiment of a steam generator of the present invention.
Figure 1B:
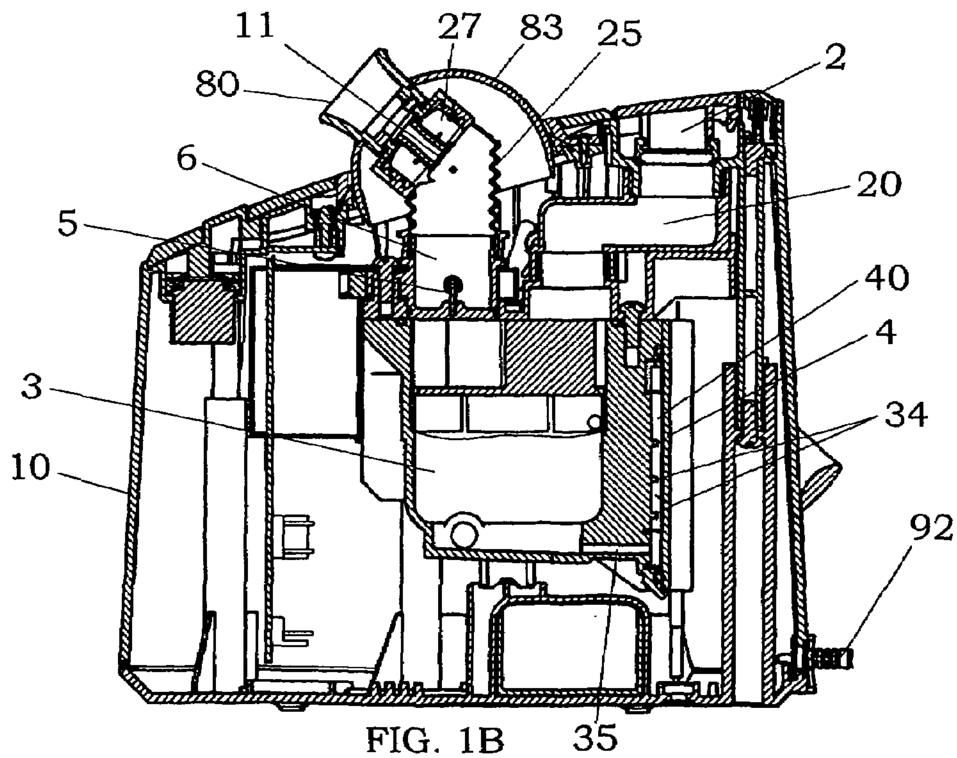

As shown in FIGS. 1A and 1B, the steam beauty machine 1 of the present embodiment is mainly composed of a housing 10 having a steam outlet 11 and a water inlet 2, a water tank 3 accommodated in the housing 10, water supply channel 20 extending between the water inlet 2 and the water tank 3, heater 4 for heating water provided from the water tank to generate steam in a steam chamber 40 formed in the housing, a steam channel 6 extending from the steam chamber 40 to the steam outlet 11, and a discharge generating portion 5 for generating a plurality of discharges in the steam channel 6. In FIG. 1A, the numeral 9 designates a protection cover for a steam nozzle 80, which is detachably attached to the steam outlet 11, and also available as a water supply vessel, as described later.

According to this steam beauty machine 1, water provided from the water tank 3 is heated to boiling by the heater 4 to generate the steam in the steam chamber 40. Then the generated steam is fed to the steam channel 6, and exposed to the discharges generated by the discharge generating portion 5, so that fine steam particles are sprayed out from the steam outlet 11. The generation of steam can be controlled by operating an ON/OFF switch 18 provided at an upper front surface of the housing 10. The ON/OFF switch 18, the heater 4 and the discharge generating portion 5 are connected to a control circuit (not shown) built in the housing, and an electric power is supplied to the control circuit through a power cable 92.

Figure 2:
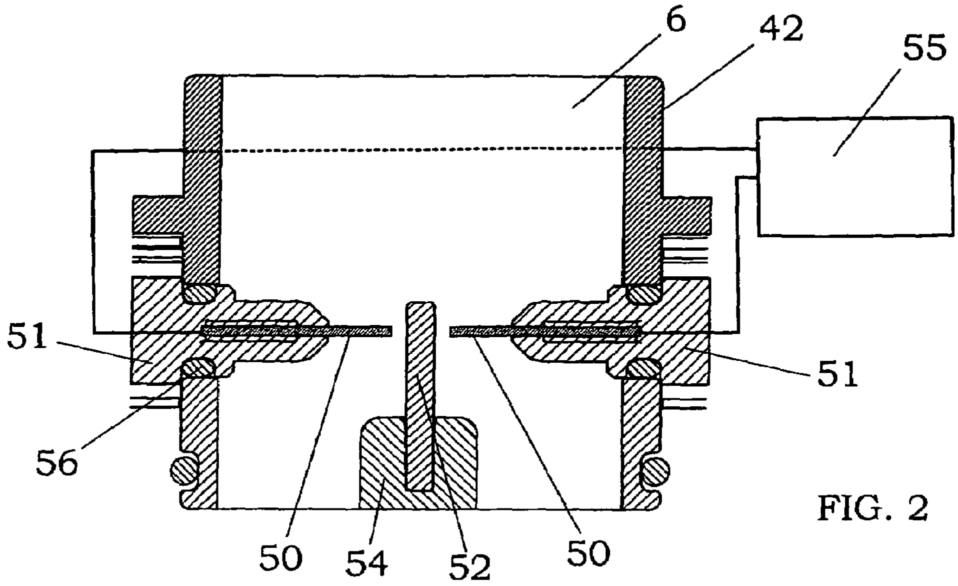
FIG. 2 is a schematic cross-sectional view of a discharge generating portion of the steam beauty machine.

As shown in FIG. 2, the discharge generating portion 5 is mainly composed of a pair of electrodes 50, intermediate electrode 52 disposed between the electrodes, and a voltage applying unit 55. Each of the electrodes 50 is a rod-like electrode supported at its one end by an electrode holder 51 fixed to a tubular member 42 used to form the steam channel 6. The electrodes 50 are disposed to have a common horizontal axis. In addition, the other ends of the electrodes 50 are in a face-to-face relation with each other through the intermediate electrode 52. The intermediate electrode 52 is a rod-like electrode supported in a standing posture by an electric holder 54 placed on a top of the water tank 3. A longitudinal axis of the intermediate electrode 52 is substantially orthogonal to the horizontal axis of the electrodes 50. Each of the electrodes 50 is disposed to face a side surface of the intermediate electrode 52. In FIG. 2, the numeral 56 designates an O-ring fitted in a groove formed in the electrode holder 51 to provide a waterproof sealing between the electrode holder 51 and the tubular member 42.

The voltage applying unit 55 applies a voltage between the electrodes 50 such that one of the electrodes is positive and the other electrode is negative. In this case, the intermediate electrode 52 is maintained in an electrically floating state. Since a distance between the intermediate electrode 52 and each of the electrodes 50 is smaller than the distance between the electrodes 50, a breakdown voltage needed to generate the discharge lowers. As a result, the discharges can be easily generated by applying a lower voltage between the electrodes 50. In addition, since two discharges are generated between the intermediate electrode 52 and the electrodes 50, generation amounts per unit time of fine steam particles can be increased. Alternatively, the voltage applying unit 55 may apply the voltage between the electrodes 50 and the intermediate electrode 52. For example, the voltage can be applied such that the electrodes 50 are positive and the intermediate electrode 52 is negative. As the voltage applied by the voltage applying unit 55, a DC voltage or AC voltage can be used. As the kind of discharge, arc discharge, corona discharge, surface discharge, or glow discharge is available. In particular, it is preferred to generate the arc discharge in the steam channel 6.

A material of the electrodes 50 is not limited on the assumption that it has electrical conductivity. To stably provide the discharge for an extended time period, it is preferred to use a material having excellent resistance to corrosion, arc resistance, and heat resistance such as a platinum group metal, platinum, gold, silver-palladium alloy, rhodium, iridium, ruthenium, copper or a conductive ceramic. As a material of the intermediate electrode 52, an electrically conductive material or an electrically insulating material can be used. In the case of using the insulating material, arc discharge is generated between the electrodes 50 and the intermediate electrode 52.

Figure 3:
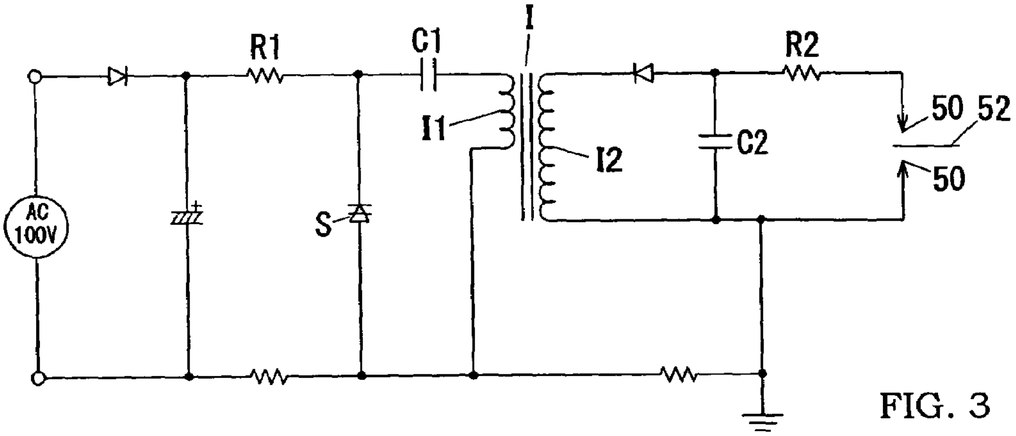
FIG. 3 is a circuit diagram of a high-voltage generating circuit.

The voltage applying unit 55 is not limited on the assumption that the discharges can be generated between the electrodes 50 and the intermediate electrode 52. For example, a high-voltage generating circuit shown in FIG. 3 can be used. According to this circuit, an input of AC 100V is rectified and smoothened, and a condenser C1 is charged through a resistance R1. When a charged voltage in the condenser C1 reaches a rated voltage of a trigger device S such as SIDAK, the trigger device is turned on, so that a large current flows in a primary winding I1 of an igniter I to generate a high voltage in a secondary winding I2 of the igniter I. Electric charges generated at this time are rectified, and stored in a condenser C2 with a high withstand voltage.

When the charged voltage in the condenser C2 reaches a predetermined voltage, the discharges are generated between the electrodes 50 and the intermediate electrode 52.

According to this high-voltage generating circuit, since the condenser C2 with the high withstand voltage is disposed at the secondary side of the igniter I, it is possible to increase amounts of electric charges at the time of generating the discharges, as compared with the case of not using the condenser C2. In addition, the product of values of the condenser C2 and a resistance R2 with a high withstand voltage provides a time constant at the time of generating the discharges. Therefore, the discharge time period can be changed by a combination of the condenser C2 and the resistance R2. That is, when the value of the condenser C2 is constant, the generation of the fine steam particles is facilitated as the value of the resistance R2 becomes smaller, in other words, the time constant becomes smaller.

In this embodiment, to increase the discharge frequency, the input of AC 100 V is rectified and smoothened, and then oscillated at 150 Hz by use of the condenser C1 and the trigger device S. By changing an amount of charged current or a capacity of the condenser C1, it is possible to appropriately determine an input frequency of the igniter, and a timing of generating the discharges. Therefore, as compared with the case of directly using a frequency (e.g., 50 or 60 Hz) of a commercial power source (e.g., AC 100V), it is possible to increase the discharge frequency.

Figure 4:
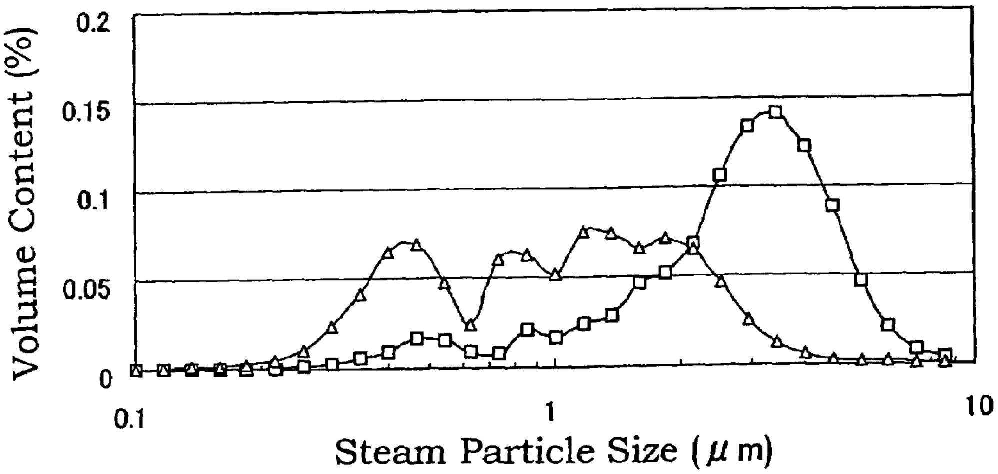
FIG. 4 is a graph showing a particle-size distribution of steam exposed to discharges.

By use of the above-described discharge generating portion 5, since two discharges are generated between the electrodes 50 and the intermediate electrode 52, it is possible to efficiently generate the fine steam particles. In FIG. 4, the symbol "□" designates a particle-size distribution of the steam exposed to a single discharge generated between a pair of electrodes, and the symbol "Δ" designates a particle-size distribution of the steam exposed to the two discharges generated between the electrodes 50 and the intermediate electrode 52. The results of FIG. 4 show that the use of the intermediate electrode 52 is effective to increase amounts of fine steam particles of 2 μm or less.

In addition, as the particle size of the steam becomes smaller, it makes the steam bleached looking. Therefore, a spraying direction of the steam from the steam nozzle 80 can be visually identified with ease. This provides improved usability of the steam beauty machine 1. As described above, the average particle size of the steam can be reduced by increasing the capacity (i.e., discharge amount) of the condenser of the discharge generating portion 5 or increasing the number of discharges generated per unit time (i.e., generating the discharge by a short discharge cycle).

In addition, as a content of relatively large steam particles (e.g., 2 to 10 μm) in the steam increases, variations in temperature of a skin surface exposed to the steam easily occur. According to the present invention, since the content of such large steam particles can be reduced by effectively increasing the content of the fine steam particles (e.g., 0.1 to 2 μm) in the steam, as shown by the symbol "Δ" in FIG. 4, it is possible to uniformly heat the skin surface with the steam, and facilitate the skin care effect.

Figure 5:
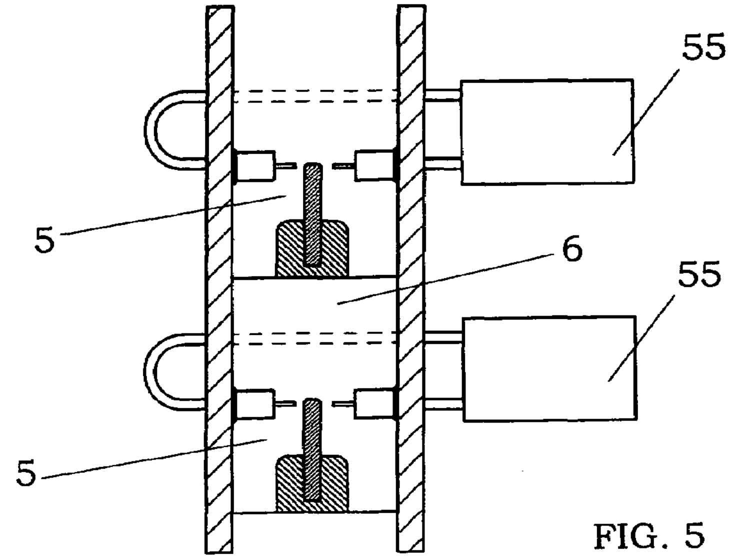
FIG. 5 is a schematic diagram of a steam channel with a pair of discharge generating portions.
Figure 6:
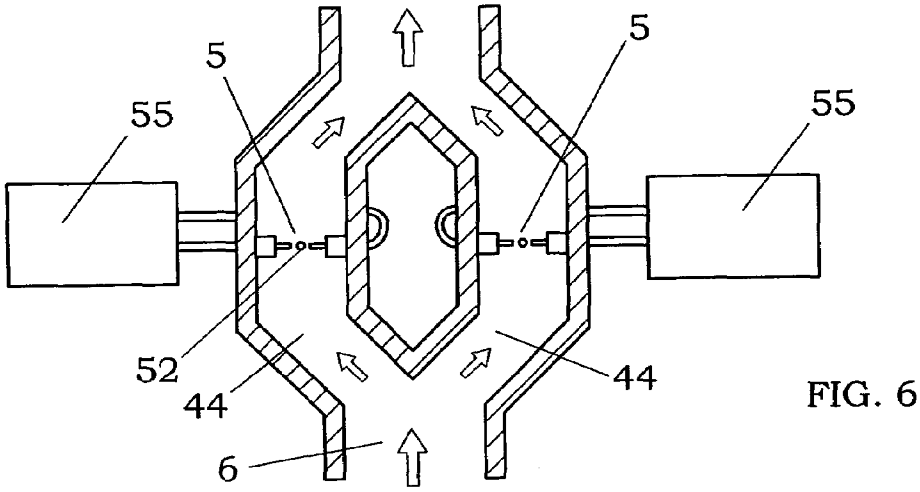
FIG. 6 is a schematic diagram of a pair of discharge channels branched from the steam channel.

To more efficiently generate the fine steam particles, it is preferred that a plurality of discharge generating portions, each of which is the same as the discharge generating portion 5 described above, are disposed in the steam channel 6, as shown in FIG. 5. In addition, as shown in FIG. 6, it is preferred that the steam channel 6 is branched into two or more discharge channels 44, in each of which the discharge generating portion 5 is formed, and these discharge channels 44 are converged at the downstream side of the discharge generating portions 5. In this case, the total amounts of the fine steam particles generated in the respective discharge channels 44 are sprayed out from the steam nozzle 80.

Figure 7:
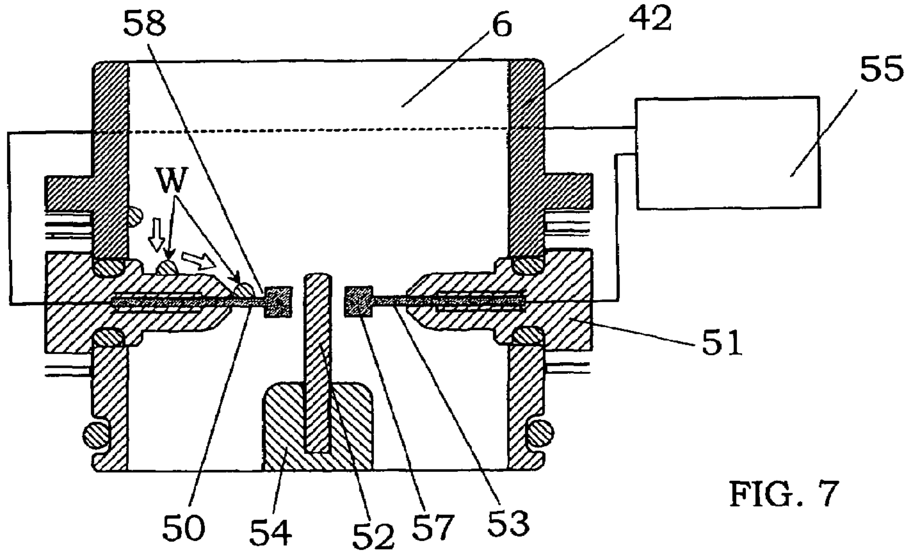
FIG. 7 is a schematic cross-sectional view of the discharge generating portion according to a modification of the embodiment.

By the way, the electrodes 50 are easily damaged at its top end portion facing the intermediate electrode 52 by repeatedly generating the discharges. To stably provide the discharges for an extended time period, it is preferred that at least one of the electrodes 50 is formed such that the top end facing the intermediate electrode 52 has a larger sectional area than the other end. For example, as shown in FIG. 7, it is preferred that each of the electrodes 50 is a rod-like electrode composed of a rod portion 53 supported at its one end by the electrode holder 51 and a head portion 57 formed at the other end of the rod portion 53 and having a larger cross section than the rod portion. In FIG. 7, the numeral 58 designates a stopper wall for preventing that a water drop W deposited on the inner surface of the steam channel 6 or the electrode holder 51 by condensation of steam flows into a discharge space between the intermediate electrode 52 and the head portion 57 through a side surface of the rod portion 53. Thus, by using this rod-like electrode, it is possible to provide the discharges in the steam channel 6 with a higher degree of reliability, and increase a life span of the electrodes 50, while minimizing an increase in electrode cost.

Figure 8:
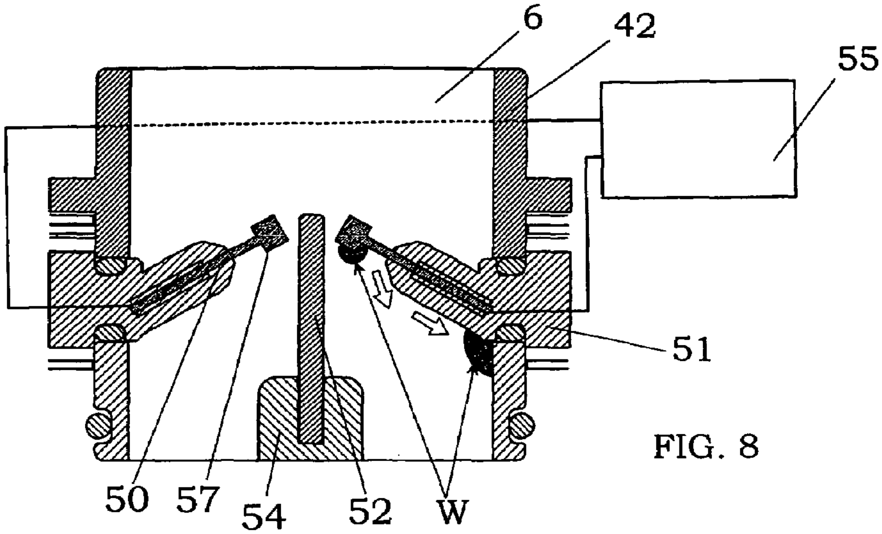
FIG. 8 is a schematic cross-sectional view of the discharge generating portion according to another modification of the embodiment.

In addition, it is preferred that at least one of the electrodes 50 is disposed in the steam channel 6 to have a down slope from its one end facing the intermediate electrode 52 toward the other end. For example, as shown in FIG. 8, the electrode 50, which is the same as the rod-like electrode shown n FIG. 7, is supported in an inclined posture by the electrode holder 51 such that the head portion 57 is located at a higher position than the side of the electrode holder. In this case, since a water drop W deposited on the electrode 50 by condensation of steam flows down toward the inner surface of the steam channel 6 through the side surface of the electrode holder 51, it is possible to prevent that that the discharge space between the electrode 50 and the intermediate electrode 52 is filled with the water drop W, and therefore further improve the stability of the discharges.

Figure 9A:
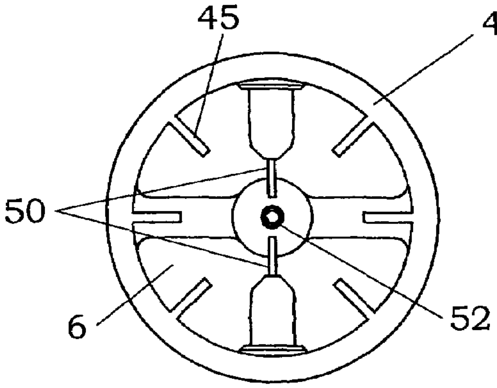
FIGS. 9A and 9B are cross-sectional views showing projection and grooves formed in the steam channel, respectively.
Figure 9B:
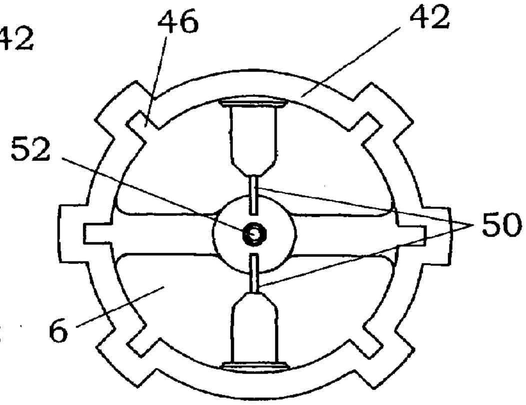
Figure 10A:
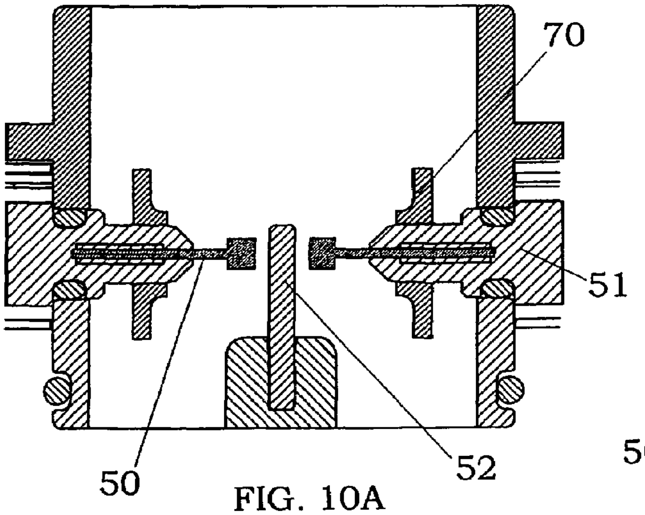
FIG. 10A is a schematic cross-sectional view of the discharge generating portion according to a further modification of the embodiment.
Figure 10B:
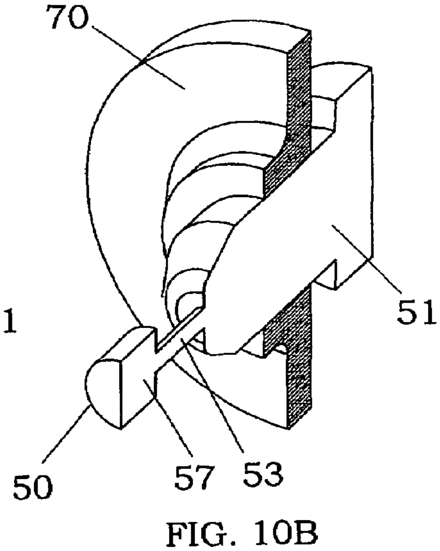
FIG. 10B is a partially cross-sectional perspective view of an electrode holder with a disk member.

To ensure electrical insulation between the electrodes 50, it is preferred that at least one of a projection 45 and a groove 46 on/in its inner surface of the tubular member 42 to increase a creepage distance for insulation, which is defined as a distance between the electrodes 50 through the inner surface of the tubular member 42. For example, as shown in FIG. 9A, the tubular member 42 has a plurality of projections 45 angularly spaced from each other. Alternatively, as shown in FIG. 9B, a plurality of grooves 46 angularly spaced from each other may be formed in the inner surface of the tubular member 42. In these cases, since the creepage distance for insulation is increased by the formation of the projections 45 and/or grooves 46, it is possible to further improve insulation reliability. In addition, it is also preferred that an insulating member is disposed in the steam channel 6 to increase the creepage distance for insulation. For example, as shown in FIGS. 10A and 10B, a disk member 70 can be attached to the electrode holder 51 to increase a surface distance between the electrode 50 and the inner surface of the steam channel 6. Furthermore, it is preferred to perform a water repellent finish to the electrode 50, the intermediate electrode 52 and/or the inner surface of the steam channel 6.

Figure 11A:
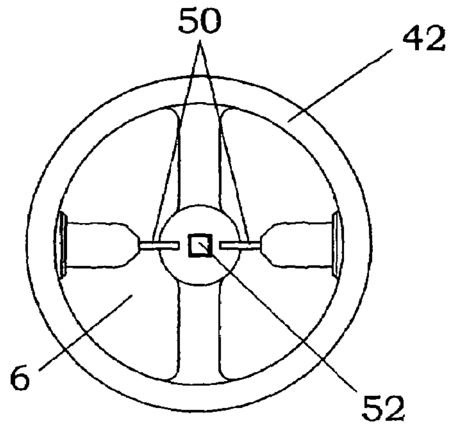
FIGS. 11A and 11B are cross-sectional views of intermediate electrodes disposed in the steam channels.
Figure 11B:
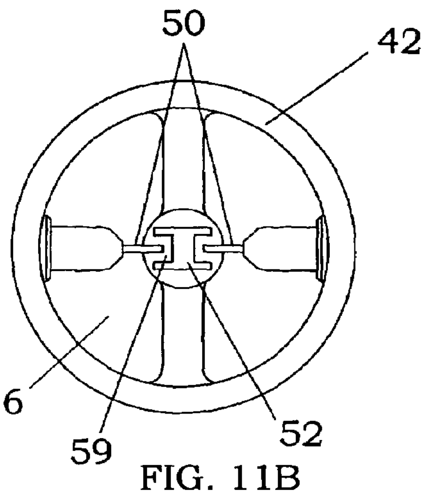

Shape of the intermediate electrode 52 is not limited. For example, as shown in FIGS. 9A and 9B, the intermediate electrode 52 has a circular cross section. In addition, as shown in FIG. 11A, the intermediate electrode 52 may have a rectangular cross section. Alternatively, it is preferred that the intermediate electrode 52 is a rod-like electrode having a substantially H-shaped cross-section. In this case, since each of the electrodes 50 is inserted in a concave 59 of the intermediate electrode 52, as shown in FIG. 11B, there is an advantage that a wide discharge area is obtained between the electrode 50 and the intermediate electrode 52.

Figure 12:
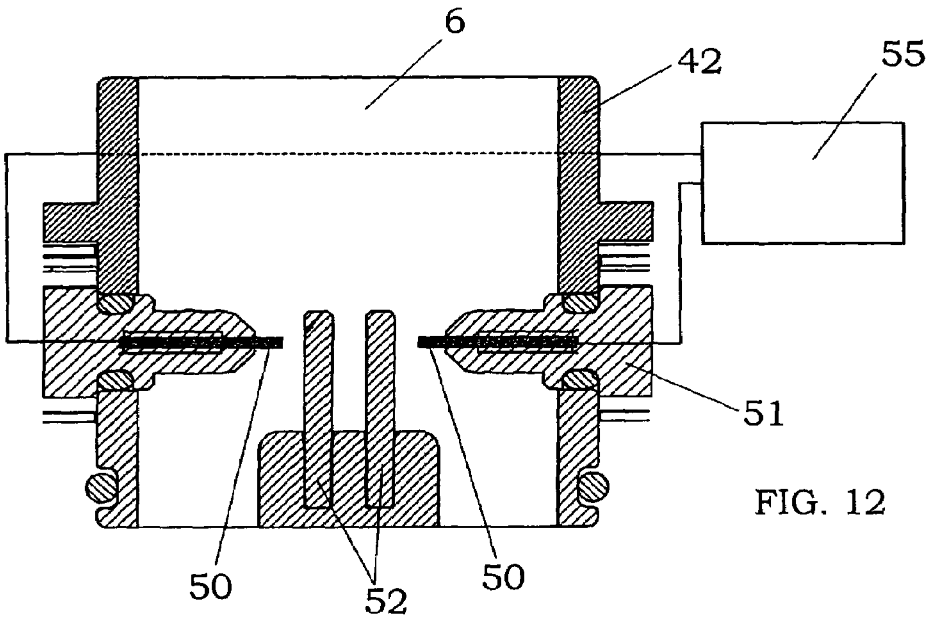
FIG. 12 is a schematic cross-sectional view of the discharge generating portion according to another modification of the embodiment.
Figure 13A:
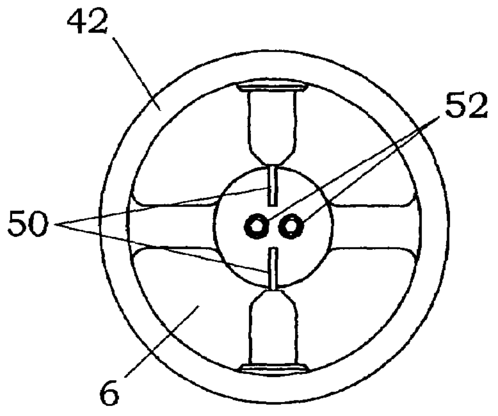
FIGS. 13A and 13B are cross-sectional views showing arrangements of a plurality of intermediate electrodes disposed in the steam channel.
Figure 13B:
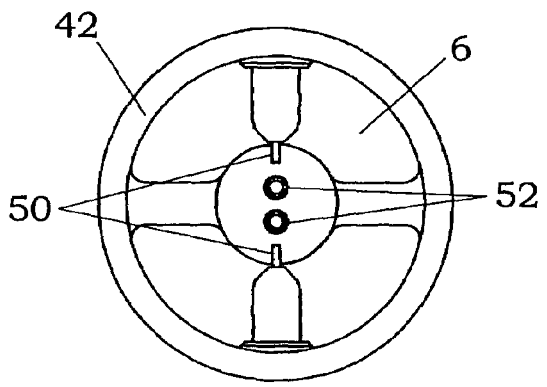

To further increase the generation amounts of the fine steam particles, it is also preferred to dispose a plurality of intermediate electrodes 52 between the electrodes 50. For example, as shown in FIG. 13A, a pair of intermediate electrodes 52 can be disposed in parallel to each other such that a direction of arrangement of the intermediate electrodes 52 is substantially orthogonal to the axial direction of the electrodes 50. Alternatively, as shown in FIGS. 12 and 13B, the pair of intermediate electrodes 52 may be disposed in parallel to each other such that the direction of arrangement of the intermediate electrodes 52 is in agreement with the axial direction of the electrodes 50. In these cases, since an increased number of discharges are generated between the electrodes 50 and the intermediate electrodes 52, it is possible to provide greater amounts of the fine steam particles through the steam nozzle 80.

To prevent that relatively large hot drops (e.g., several ten microns) of water generated in the steam chamber 40 is fed to the discharge generating portion 5, it is preferred to dispose a partition wall(s) with a required pattern in the steam channel 6. For example, as shown in FIG. 14, a T-shaped partition wall 48 can be disposed in the steam channel 6 between the steam chamber 40 and the discharge generating portion 5. In this case, the steam generated in the steam chamber 40 is fed to the discharge generating portion 5 through clearances between the T-shaped partition wall 48 and the inner surface of the steam channel 6. The hot water drops trapped on the partition wall 48 or an inner surface of the steam channel 6 are returned to the water tank 3 through apertures 47. In addition, it is preferred to dispose a filter at a coupling portion between the steam chamber 40 and the steam channel 6.

To efficiently supply the steam particles to the discharge generating portion 5, it is preferred that the steam chamber 40 is provided by an elongate clearance extending in a height direction between an outer side surface of the water tank 3 and the heater 4, as shown in FIG. 1B. In this case, the steam generated in the steam chamber 40 is fed to the steam channel 6 through an opening formed in an upper portion of the steam chamber 40. It is also preferred that a plurality of bosses 34 are formed on the outer side surface of the water tank 3 in the steam chamber 40 such that they are spaced from each other in the height direction.

In this embodiment, to prevent that water rapidly flows from the water tank 3 into the steam chamber 40, a communication channel 35 having a relatively long axial length and a narrow cross section is formed between the water tank 3 and the steam chamber 40. When the communication channel 35 is configured to have a circular cylindrical shape, a diameter of the communication channel is preferably determined to be sufficiently smaller than the axial length. For example, the diameter and the axial length of the communication channel 35 are 2.5 mm and 18.0 mm, respectively.

In addition, it is preferred to dispose a filter at the vicinity of an exit of the communication channel 35 in the steam chamber 40 to remove scales such as calcium carbonate deposited by volatilization of water. It is also effective to prevent clogging of the communication channel 35 or contamination of the water tank 3 with the scales. It is preferred that the filter has a mesh size equal to or smaller than 50% of the diameter of the communication channel 35. In this embodiment, the diameter of the communication channel 35 is 2.5 mm, and the mesh size of the filter is 1.0 mm, which corresponds to 40% of the diameter of the communication channel 35.

In this embodiment, the steam channel 6 is provided at the downstream side of the discharge generating portion 5 by an accordion hose 25, as shown in FIG. 1. The steam nozzle 80 is connected to a top open end of the accordion hose 25 through a joint member 27. The steam nozzle 80 is also coupled to a dome-like shell 83, which is movably supported to the housing 10. Therefore, it is possible to safely change the steam spraying direction over a wide angular range, while protecting the steam channel 6 with the dome-like shell 83. In addition, since hot water drops formed by condensation of the steam are efficiently trapped by a rugged inner surface of the accordion hose 25, it is possible to prevent that the hot water drops are accidentally jetted out from the steam nozzle 80, and further improve the safety of the steam beauty machine 1. To prevent a water leakage in the case that the beauty machine is accidentally toppled over, a water absorbing means such as sponge may be disposed in the vicinity of the joint member 27.

As described above, since the protection cover 9 for the steam nozzle 80 is configured in a concave shape, it can be used as the water supply vessel such as a water pot for supplying water into the water tank 3 through the water inlet 2. As shown in FIGS. 15A to 15C, the protection cover 9 has a pour spout 95 having an appropriate open area to provide a smooth water flow to the water inlet 2, and an overflow stopper 93 provided above the pour spout 95 to prevent that a large amount of water rapidly flows into the water inlet 2. For example, the pour spout 95 can be configured in a rectangular shape having a side of 10 mm.

As understood from the above preferred embodiment, according to the present invention, it is possible to provide a steam generator having the capability of efficiently generating fine steam particles of 2 μm or less, which is preferably used as the steam beauty machine, by disposing at least one intermediate electrode between the electrodes of the discharge generating portion.

What is claimed is:

1. A steam generator comprising:

a housing having a steam outlet;

a liquid tank for storing a liquid;

a heater for heating the liquid provided from said liquid tank to generate steam in a chamber formed in said housing;

a steam channel extending from said chamber to said steam outlet;

at least one pair of electrodes disposed in said steam channel;

at least one intermediate electrode disposed between said electrodes; and a discharge generator configured to generate discharges between each of said electrodes and said at least one intermediate electrode.

2. The steam generator as set forth in claim 1, wherein said discharge generator is a voltage applying means for applying a voltage between said electrodes, while keeping said at least one intermediate electrode in an electrically floating state.

3. The steam generator as set forth in claim 1, wherein said discharge generator is a voltage applying means for applying a voltage between said at least one intermediate electrode and said electrodes.

4. The steam generator as set forth in claim 1, further comprising a filter for preventing that steam particles having diameters greater than a predetermined value flow from said chamber into said steam channel.

5. The steam generator as set forth in claim 1, wherein at least one of said electrodes is formed such that its one end facing said at least one intermediate electrode has a larger sectional area than the other end.

6. The steam generator as set forth in claim 1, wherein at least one of said electrodes has a stopper for preventing that a drop of said liquid flows into a discharge space between said at least one intermediate electrode and said electrode.

7. The steam generator as set forth in claim 1, wherein at least one of said electrodes is disposed to have a down slope from its one end facing said at least one intermediate electrode toward the other end.

8. The steam generator as set forth in claim 1, wherein said steam channel is formed by a tubular member having at least one of a projection and a groove on/in its inner surface to increase a creepage distance for insulation between said electrodes.

9. The steam generator as set forth in claim 1, further comprising an insulating member disposed in said steam channel to increase a creepage distance for insulation between said electrodes.

10. The steam generator as set forth in claim 1, wherein each of said electrodes is disposed such that its top end faces a side of said at least one intermediate electrode.

11. The steam generator as set forth in claim 1, wherein said at least one intermediate electrode is a plurality of intermediate electrodes, which are spaced from each other between said electrodes.

12. The steam generator as set forth in claim 1, wherein said at least one intermediate electrode is a rod-like electrode having a substantially H-shaped cross-section.

* * * * *